United States Patent
Govari et al.

(10) Patent No.: US 12,285,206 B2
(45) Date of Patent: Apr. 29, 2025

(54) APPLICATION OF IRREVERSIBLE ELECTROPORATION (IRE) ABLATION USING CATHETER WITH ELECTRODE ARRAY

(71) Applicant: BIOSENSE WEBSTER (ISRAEL) LTD., Yokneam (IL)

(72) Inventors: Assaf Govari, Haifa (IL); Andres Claudio Altmann, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 169 days.

(21) Appl. No.: 16/889,565

(22) Filed: Jun. 1, 2020

(65) Prior Publication Data
US 2021/0369338 A1    Dec. 2, 2021

(51) Int. Cl.
A61B 18/14    (2006.01)
A61B 18/00    (2006.01)
A61B 90/00    (2016.01)

(52) U.S. Cl.
CPC .......... *A61B 18/1492* (2013.01); *A61B 2018/00267* (2013.01); *A61B 2018/00613* (2013.01);
(Continued)

(58) Field of Classification Search
CPC ...... A61B 18/1492; A61B 2018/00267; A61B 2018/00613; A61B 2018/00875; A61B 2018/1467; A61B 2090/065; A61B 2018/00023; A61B 2018/00029; A61B 2018/0016; A61B 2018/00351; A61B 2018/00654; A61B 2018/00839;
(Continued)

(56) References Cited

U.S. PATENT DOCUMENTS 5,391,199 A    2/1995    Ben Haim
5,704,908 A    1/1998    Hofmann
(Continued)

FOREIGN PATENT DOCUMENTS

JP    2018187373 A    11/2018
JP    2018537136 A    12/2018
(Continued)

OTHER PUBLICATIONS

Search Report from corresponding Japanese Patent Application No. 2021-056876 dated Sep. 27, 2024.

*Primary Examiner* — Khadijeh A Vahdat
*Assistant Examiner* — Marina Delaney Templeton
(74) *Attorney, Agent, or Firm* — Dergosits & Noah LLP; Todd A. Noah

(57) ABSTRACT

A method includes inserting an array of multiple electrodes, fitted at a distal end of a catheter, into a cavity in an organ of a patient. The array is brought into contact with an inner surface of the cavity. An input is received from a user, the input specifying one or more tissue segments to be ablated on the inner surface. In response to the input, using a processor, one or more pairs of the electrodes in the array are selected that, when driven with irreversible electroporation (IRE) signals, would ablate the specified tissue segments. The specified tissue segments are ablated by applying the IRE signals to the pairs of the electrodes.

13 Claims, 3 Drawing Sheets

(52) U.S. Cl.
CPC ............... *A61B 2018/00875* (2013.01); *A61B 2018/1467* (2013.01); *A61B 2090/065* (2016.02)

(58) Field of Classification Search
CPC .... A61B 2018/00904; A61B 2018/126; A61B 2218/002; A61B 18/1206; A61B 2018/00577; A61B 2018/00642; A61B 2018/00702; A61B 34/10; A61B 18/1815; A61B 18/18; A61B 2018/00791
See application file for complete search history.

(56) References Cited

U.S. PATENT DOCUMENTS

| | | | | |
|---|---|---|---|---|
| 5,759,158 | A * | 6/1998 | Swanson | A61B 5/6858 600/508 |
| 6,014,581 | A * | 1/2000 | Whayne | A61B 5/6858 600/523 |
| 6,239,724 | B1 | 5/2001 | Doron | |
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben Haim | |
| 7,326,204 | B2 * | 2/2008 | Paul | A61B 18/1402 606/41 |
| 7,756,576 | B2 | 7/2010 | Levin | |
| 7,848,787 | B2 | 12/2010 | Osadchy | |
| 7,869,865 | B2 | 1/2011 | Govari | |
| 8,048,067 | B2 | 11/2011 | Davalos | |
| 8,221,411 | B2 | 7/2012 | Francischelli | |
| 8,880,195 | B2 * | 11/2014 | Azure | A61B 18/1477 607/148 |
| 9,867,978 | B1 | 1/2018 | Rapoport et al. | |
| 9,987,081 | B1 * | 6/2018 | Bowers | A61N 1/327 |
| 10,271,893 | B2 | 4/2019 | Stewart | |
| 10,342,598 | B2 | 7/2019 | Long | |
| 10,531,914 | B2 | 1/2020 | Stewart | |
| 10,675,462 | B2 | 6/2020 | He et al. | |
| 10,842,572 | B1 * | 11/2020 | Viswanathan | A61B 34/10 |
| 2002/0065455 | A1 | 5/2002 | Ben Haim | |
| 2002/0077627 | A1 * | 6/2002 | Johnson | A61B 18/1477 606/41 |
| 2003/0120150 | A1 | 6/2003 | Govari | |
| 2003/0130711 | A1 * | 7/2003 | Pearson | A61B 18/1477 607/101 |
| 2004/0068178 | A1 | 4/2004 | Govari | |
| 2005/0065509 | A1 | 3/2005 | Coldwell | |
| 2006/0293713 | A1 * | 12/2006 | Rubinsky | A61N 1/327 607/2 |
| 2008/0097559 | A1 * | 4/2008 | Eggers | A61B 18/14 607/102 |
| 2008/0255642 | A1 * | 10/2008 | Zarins | A61N 7/02 607/99 |
| 2009/0062788 | A1 * | 3/2009 | Long | A61B 18/14 606/41 |
| 2010/0087813 | A1 * | 4/2010 | Long | A61B 1/06 606/41 |
| 2010/0204560 | A1 * | 8/2010 | Salahieh | A61B 5/01 606/41 |
| 2011/0160514 | A1 * | 6/2011 | Long | A61B 18/1477 606/41 |
| 2011/0301587 | A1 * | 12/2011 | Deem | A61B 18/1815 606/41 |
| 2012/0059255 | A1 * | 3/2012 | Paul | A61N 1/327 600/431 |
| 2012/0071870 | A1 * | 3/2012 | Salahieh | A61B 1/00082 606/33 |
| 2012/0310230 | A1 * | 12/2012 | Willis | A61N 1/327 606/41 |
| 2013/0090646 | A1 * | 4/2013 | Moss | A61B 18/1815 606/41 |
| 2013/0184702 | A1 * | 7/2013 | Neal | A61B 18/00 606/41 |
| 2013/0218157 | A1 | 8/2013 | Callas | |
| 2014/0012247 | A1 | 1/2014 | Bakos | |
| 2016/0051324 | A1 | 2/2016 | Stewart | |
| 2016/0113707 | A1 * | 4/2016 | Sahakian | A61B 18/1477 606/41 |
| 2016/0113709 | A1 * | 4/2016 | Maor | A61B 18/1492 606/41 |
| 2016/0331446 | A1 * | 11/2016 | Martin | A61B 18/1492 |
| 2017/0043154 | A1 | 2/2017 | Pelssers et al. | |
| 2017/0119465 | A1 | 5/2017 | Long | |
| 2017/0120048 | A1 | 5/2017 | He | |
| 2017/0189106 | A1 * | 7/2017 | Schuler | A61B 5/00 |
| 2017/0348049 | A1 * | 12/2017 | Vrba | A61B 18/1492 |
| 2018/0071014 | A1 * | 3/2018 | Neal | A61M 25/00 |
| 2018/0116751 | A1 * | 5/2018 | Schwartz | G06F 30/20 |
| 2018/0228528 | A1 * | 8/2018 | Fraasch | A61B 18/1233 |
| 2018/0296277 | A1 * | 10/2018 | Schwartz | G06F 30/20 |
| 2018/0310987 | A1 * | 11/2018 | Altmann | A61B 18/1492 |
| 2018/0311497 | A1 * | 11/2018 | Viswanathan | A61N 1/327 |
| 2019/0030328 | A1 * | 1/2019 | Stewart | A61B 18/1492 |
| 2019/0201040 | A1 * | 7/2019 | Messerly | A61B 17/320092 |
| 2019/0223949 | A1 * | 7/2019 | Coates | A61B 18/1492 |
| 2019/0328274 | A1 | 10/2019 | Gliner et al. | |
| 2019/0350649 | A1 | 11/2019 | Sutermeister | |
| 2019/0365463 | A1 | 12/2019 | Govari | |
| 2020/0015876 | A1 * | 1/2020 | Chou | A61B 18/00 |
| 2020/0022653 | A1 * | 1/2020 | Moisa | A61B 5/066 |
| 2020/0397505 | A1 * | 12/2020 | Viswanathan | A61B 34/20 |
| 2021/0113265 | A1 * | 4/2021 | D'Agostino | A61B 18/082 |
| 2021/0137587 | A1 * | 5/2021 | Olson | A61B 18/1206 |
| 2021/0169394 | A1 * | 6/2021 | Chou | G16H 50/30 |
| 2021/0322093 | A1 | 10/2021 | Govari et al. | |
| 2022/0008123 | A1 * | 1/2022 | Altmann | A61B 18/1492 |
| 2022/0071681 | A1 * | 3/2022 | Rupp | A61B 18/1492 |
| 2023/0320784 | A1 | 10/2023 | Thiel et al. | |

FOREIGN PATENT DOCUMENTS

| | | |
|---|---|---|
| RU | 2016147150 A | 6/2018 |
| RU | 2018118953 A | 11/2019 |
| WO | WO1996005768 A1 | 2/1996 |
| WO | WO1999037358 A1 | 7/1999 |
| WO | WO2018191149 A1 | 10/2018 |

* cited by examiner

APPLICATION OF IRREVERSIBLE ELECTROPORATION (IRE) ABLATION USING CATHETER WITH ELECTRODE ARRAY

FIELD OF THE INVENTION

The present invention relates generally to medical probes, and particularly to multi-electrode catheters.

BACKGROUND OF THE INVENTION

Various medical probes having multiple electrodes disposed over their distal-end are proposed in the patent literature. For example, U.S. Pat. No. 9,867,978 describes an array of electrodes on a flexible scaffolding, with the ability to collapse into an axial configuration suitable for deploying through a narrow cylindrical channel. The electrode arrays can be placed into the ventricular system of the brain, constituting a minimally invasive platform for precise spatial and temporal localization of electrical activity within the brain, and precise electrical stimulation of brain tissue, to diagnose and restore function in conditions caused by abnormal electrical activity in the brain.

As another example, U.S. Patent Application Publication No. 2005/0065509 describes an apparatus for ablating pleurae with electrical energy, which includes an array of electrodes disposed within a lumen of a cannula and deployable from a distal end of the cannula. The electrodes may extend in a direction substantially perpendicular to a longitudinal axis of the cannula when deployed from the cannula, thereby defining a plane. During use, the cannula may be inserted into a thoracic cavity until the distal end is adjacent the pleura. The electrodes are advanced from the cannula such that distal portions of the electrodes extend away from one another and lie within a plane. The distal portions are placed in contact with the pleura, and electrical energy is delivered from the electrodes to ablate the pleura.

SUMMARY OF THE INVENTION

An embodiment of the present invention that is described hereinafter provides a method including inserting an array of multiple electrodes, fitted at a distal end of a catheter, into a cavity in an organ of a patient. The array is brought into contact with an inner surface of the cavity. An input is received from a user, the input specifying one or more tissue segments to be ablated on the inner surface. In response to the input, using a processor, one or more pairs of the electrodes in the array are selected that, when driven with irreversible electroporation (IRE) signals, would ablate the specified tissue segments. The specified tissue segments are ablated by applying the IRE signals to the pairs of the electrodes.

In some embodiments, receiving the input includes visualizing to the user a position of the array relative to the cavity, and receiving the input in response to the visualized position.

In some embodiments, receiving the input includes indicating to the user a partial subset of the electrodes in the array that are in contact with the inner surface of the cavity, and receiving the input in response to the subset.

In other embodiments, receiving the input includes indicating to the user one or more regions on the inner surface of the cavity that are in contact with the array, and receiving the input in response to the one or more regions.

In an embodiment, bringing the array into contact with the inner surface of the cavity includes measuring impedances using the multiple electrodes.

In another embodiment, bringing the array into contact with the inner surface of the cavity includes measuring a shape of the array. In yet another embodiment, bringing the array into contact with the inner surface of the cavity includes measuring contact force between the array and the surface.

In some embodiments, the array is a flat array.

There is additionally provided, in accordance with another embodiment of the present invention, a system including a processor and an IRE generator. The processor is connected to an array of multiple electrodes that is fitted at a distal end of a catheter, inserted into a cavity in an organ of a patient and brought into contact with an inner surface of the cavity, with the processor configured to: (a) receive, from a user, input that specifies one or more tissue segments to be ablated on the inner surface of the cavity, and (b) select one or more pairs of the electrodes in the array that, when driven with irreversible electroporation (IRE) signals, would ablate the specified tissue segments. The IRE generator is configured to ablate the specified tissue segments by applying the IRE signals to the pairs of the electrodes.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
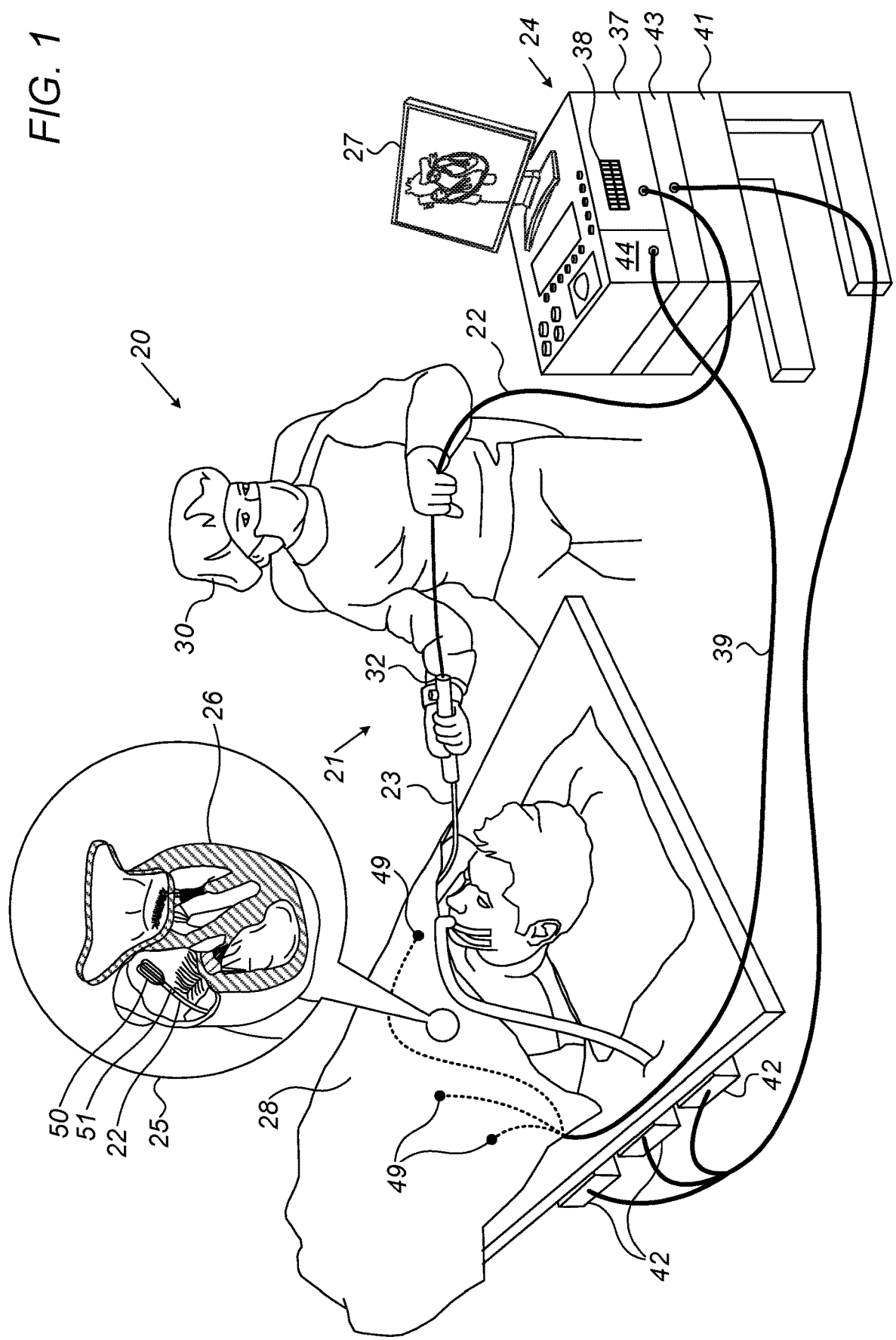
FIG. 1 is a schematic, pictorial illustration of a catheter-based irreversible electroporation (IRE) ablation system comprising a flat array of multiple electrodes, in accordance with an exemplary embodiment of the present invention.

Irreversible electroporation (IRE), also called Pulsed Field Ablation (PFA), may be used as an invasive therapeutic modality to kill tissue cells of surface tissue of a cavity of an organ of a patient by subjecting them to high-voltage pulses. Specifically, IRE pulses have a potential use to kill myocardium tissue cells (e.g., of a cardiac chamber) in order to treat cardiac arrhythmia. Of particular interest is the use of bipolar electric pulses (e.g., using a pair of electrodes of a catheter in contact with tissue) to kill tissue cells between the electrodes. Cellular destruction occurs when the transmembrane potential exceeds a threshold, leading to cell death and thus the development of a tissue lesion.

In order for IRE to be used effectively to ablate selected tissue, it is important to be able to bring the electrodes providing the IRE pulses in contact with selected tissue. While this is possible with substantially any catheter, such as a focal or a basket catheter, if large areas of tissue are to be ablated these catheter types need to be moved so that the electrodes are correctly positioned. Moreover, the electrodes need to maintain contact with the surface tissue during cardiac wall movement, which, in particular, may increase complexity and the time required to complete the ablation.

Using multiple electrodes that are simultaneously positioned in close proximity to one another, and in contact with the surface tissue, can increase the effectiveness of the IRE ablation by strengthening an applied electric field, and, optionally, by locally controlling a direction of the electric field to achieve better selectivity in favor of irreversibly electroporating cardiac cells only.

Exemplary embodiments of the present invention that are described hereinafter use an array catheter, such as a flat array catheter, with a large number of electrodes, for applying the IRE pulses to an inner surface of a cavity in an organ of a patient, to which the flat array is inserted.

In an exemplary embodiment, a physician inserts the array, fitted at a distal end of a catheter, into the cavity, and brings the array into contact with the inner surface of the cavity. The physician specifies one or more tissue segments to be ablated on the inner surface. In response to the input, a processor selects one or more pairs of the electrodes in the array that, when driven with IRE signals, would ablate the specified tissue segments. An IRE pulse generator that the processor controls, ablates the specified segments by applying the IRE signals to the pairs of the electrodes.

In some exemplary embodiments the array is flat, while in other exemplary embodiments the array is curved, such as an array of a basket catheter. The array is typically two-dimensional but may be one-dimensional.

In one exemplary embodiment, the input from the physician (i.e., user) is based on a visualization to the physician of a position of the array relative to the cavity. In another exemplary embodiment, the user receives as an input a partial subset of the electrodes in the array that are in contact with the inner surface of the cavity. In yet another exemplary embodiment, the user receives as an input indication of one or more regions on the inner surface of the cavity that are in contact with the array.

In an exemplary embodiment, the physician receives an indication regarding which electrodes of the catheter's electrode array are in contact with tissue, e.g., using a method to determine if a catheter electrode is in physical contact with tissue by measuring a frequency-response of the electrode for example, as described in U.S. Patent Application Publication No. 2019/0365463 assigned to Biosense Webster, and then selecting at least these electrodes of the array, as described below.

In another exemplary embodiment, using the typically large areas of the disclosed arrays of electrodes, a physician may simultaneously ablate separate tissue regions deemed in contact with electrodes of the array, for example, by selecting a subset of the electrodes per each region.

In one exemplary embodiment, the electrodes are formed as short cylinders on tubes, with insulated leads for the electrodes within the tubes, and the tubes deployed in a "fly-swatter" format such as with the Picasso™ catheter, made by Biosense-Webster, California. By forming the electrodes as relatively massive cylinders around the tubes, the electrodes are able to transfer the high IRE voltages without themselves being destroyed. Irrigation fluid can also be conveyed through the tubes to cool electrode edges in order to avoid voltage breakdowns.

In another exemplary embodiment, the electrodes are formed over an expandable flexible distal-end assembly which comprises two flexible substrates upon which is printed an array of electrodes, together with conductors to the electrodes. The substrates are cemented on either side of a flat flexible Nitinol backing sheet, within which irrigation channels are formed. The irrigation is performed by flowing a coolant into blood in the vicinity of the electrodes via holes in the substrates connected to the channels.

Alternatively, a cooling fluid may circulate in a closed loop in channels having thermal contact with blood. Expandable flexible distal-end assemblies with the two cooling options are described in U.S. patent application Ser. No. 16/852,165, filed Apr. 17, 2020, and titled, "Flexible Distal-End Assembly with Double-Sided Electrode Array and Irrigation," whose disclosure is incorporated herein by reference.

In the disclosed method, the catheter is navigated to a desired section of tissue using an electrical tracking system and/or a magnetic tracking system. Once in its location, the physician using the catheter utilizes a provided protocol to select which electrodes are to be used for the IRE ablation, as well as the parameters of the IRE pulses.

By using an array (e.g., a flat array) catheter and by selecting pairs of electrodes and IRE parameters, the disclosed method can yield an efficient and consistent ablation over a wide area and in complicated tissue anatomy.

System Description

FIG. 1 is a schematic, pictorial illustration of a catheter-based irreversible electroporation (IRE) ablation system 20 comprising a flat electrode-array catheter 21, in accordance with an exemplary embodiment of the present invention. System 20 is used to determine the position of a flat array 50 of multiple electrodes 55 (FIG. 2), by way of example, the aforementioned Picasso™ catheter, seen in an inset 25 fitted at a distal end of a shaft 22, to IRE ablate target cardiac tissue of a heart 26 of a patient 28.

Physician 30 navigates flat array 50 to the target tissue location in heart 26 by manipulating shaft 22 using a manipulator 32 near the proximal end of the catheter and/or deflection from a sheath 23. Flat array 50 is inserted through sheath 23 in a folded configuration, and only after sheath 23 is retracted does flat array 50 regain its intended functional shape. By containing flat array 50 in a folded configuration, sheath 23 also serves to minimize vascular trauma along the way to target location.

Typically, flat array 50 is used for diagnostic or therapeutic treatment, such as spatially mapping the heart and mapping respective electrical potentials in the heart prior to performing an ablation of heart tissue.

As noted above, flat array 50 comprises multiple electrodes (seen in FIG. 2) disposed over a large area assembly of electrodes, and have multiple uses (i.e., navigation, sensing, and ablation). The electrodes are connected by wires running through shaft 22 to an IRE pulse generator 37 comprising a processor-controlled switching circuitry 38 (e.g., an array of relays) in a console 24. Using circuitry 38, a system processor, or the physician, may select which electrodes to connect to pulse-generator 37 to apply IRE pulses.

Console 24 comprises a processor 41, typically a general-purpose computer, with suitable front end and interface circuits 44 for receiving signals from patch electrodes 49. Signals from electrodes 49 may be electrocardiograms (ECG) and/or position signals used in an Advanced Catheter Location (ACL) catheter-position tracking method described below. Processor 41 is connected to patch electrodes 49, which are attached to the skin of the chest of patient 26, by wires running through a cable 39.

In some exemplary embodiments, processor 41 accurately determines position coordinates of the electrodes of flat electrode-array 50 inside heart 26. Processor 41 determines the position coordinates based on, among other inputs, measured impedances between the electrodes (on the catheter) and ACL patch electrodes 49 (i.e., using the ACL method described below). Console 24 drives a display 27 which shows the distal end of catheter position inside the heart.

Processor 41, upon calculating an estimated location of at least a portion of the electrodes of flat array 50 within the patient's heart, may then associate any given signal received from the electrodes, such as an electrophysiological signal, with the location at which the signal was acquired.

The ACL method of electrode position sensing using system 20 is implemented in various medical applications, for example in the CARTO™ system, produced by Biosense Webster Inc. (Irvine, California) and is described in detail in U.S. Pat. Nos. 7,756,576, 7,869,865, and 7,848,787, whose disclosures are all incorporated herein by reference.

Console 24 further comprises a magnetic-sensing subsystem. Patient 28 is placed in a magnetic field generated by a pad containing magnetic field generator coils 42, which are driven by unit 43. The magnetic fields generated by coils 42 generate position signals in a magnetic sensor 51, seen in inset 25 fitted just proximally to flat array 50. The signals are further provided as corresponding electrical inputs to processor 41, which uses them to calculate, for example, a roll angle of flat array 50 to correct the ACL-derived electrode positions and/or orientation of the flat array inside the cavity.

The method of position sensing using external magnetic fields is implemented in various medical applications, for example, in the CARTO™ system, produced by Biosense Webster Inc. (Irvine, California) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs dedicated algorithms that enable processor 41 to perform the steps shown in FIG. 4.

FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description. Another position tracking technique that can be used for tracking the locations of the electrodes on flat array 50 inside heart 26, similar to the ACL described above, is described in U.S. patent application Ser. No. 15/966,514, filed Apr. 30, 2018, titled "Improved Active Voltage Location (AVL) Resolution," which is assigned to the assignee of the present patent application, which document is incorporated by reference herein.

Flexible Distal-End Assembly for Double-Layer Electrode Array and Irrigation

Figure 2:
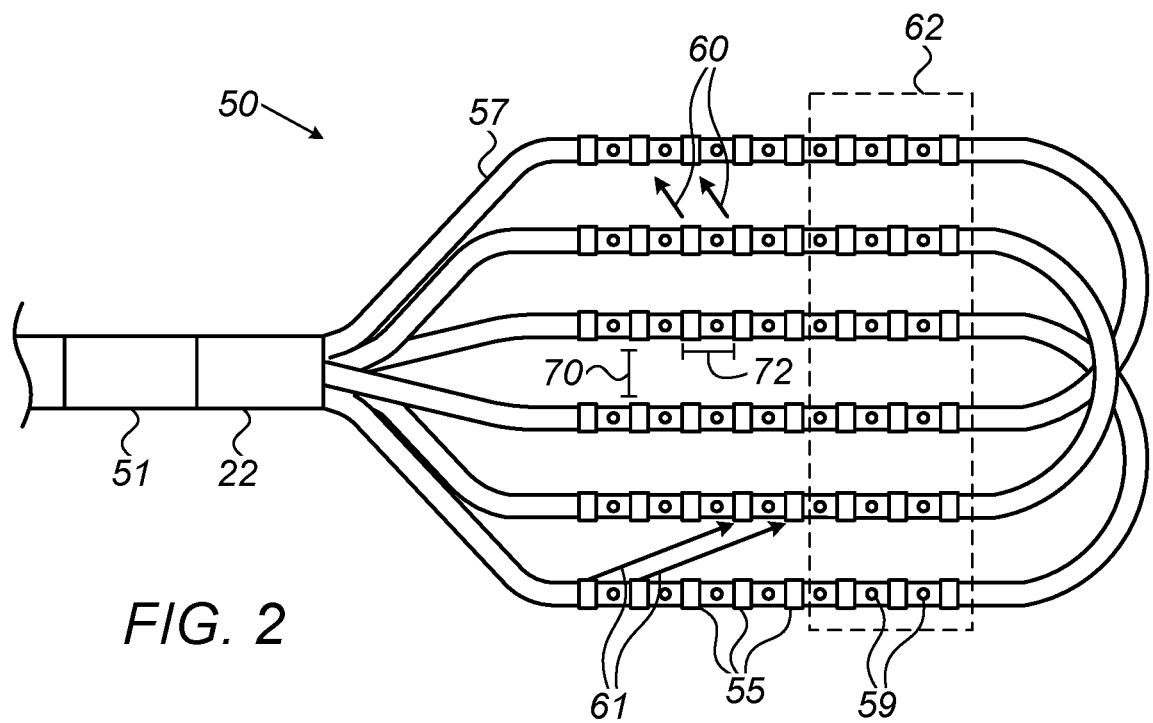
FIG. 2 is a side view of the flat array of multiple electrodes, of the catheter of FIG. 1, in accordance with an exemplary embodiment of the present invention.

FIG. 2 is a side view of flat array 50 of multiple electrodes 55, of catheter 21 of FIG. 1, in accordance with exemplary embodiments of the present invention. The shown electrode-array assembly (i.e., flat array of electrodes) is that of the aforementioned Picasso™ catheter, though, as noted above, other flat electrode-array assemblies may be used.

As seen, flat array 50 comprises an array of cylindrical electrodes 55 fitted over tubes 57. The array is characterized by inter-electrode distances 70 and 72, which, for a given voltage of a bipolar electrical pulse that falls between any two electrodes 55, determines a strength of the electric field applied to tissue between them. Moreover, as seen by field lines 60 and 61, electrode pairs can be selected according to a direction of the electric field that is deemed best suitable, e.g., for killing myocardium cells with higher selectively.

FIG. 2 describes schematically a region 62 that includes a subset of electrodes 55, which are selected for applying IRE ablation using processor 41 that commands switching circuitry 38. Anatomy-driven and/or physiology-driven selection, and the use of subsets of the electrodes 55 for IRE ablation, are described in relation to FIG. 3.

Finally, cooling fluid is conveyed through tubes 57 to electrode edges to avoid voltage breakdowns. The cooling fluid may circulate in a closed loop, or, optionally, the tubes may include irrigation holes 59 to flow (i.e., irrigate) cooling fluid (e.g., saline solution) into blood in the vicinity of the edges of the electrodes.

Figure 3:
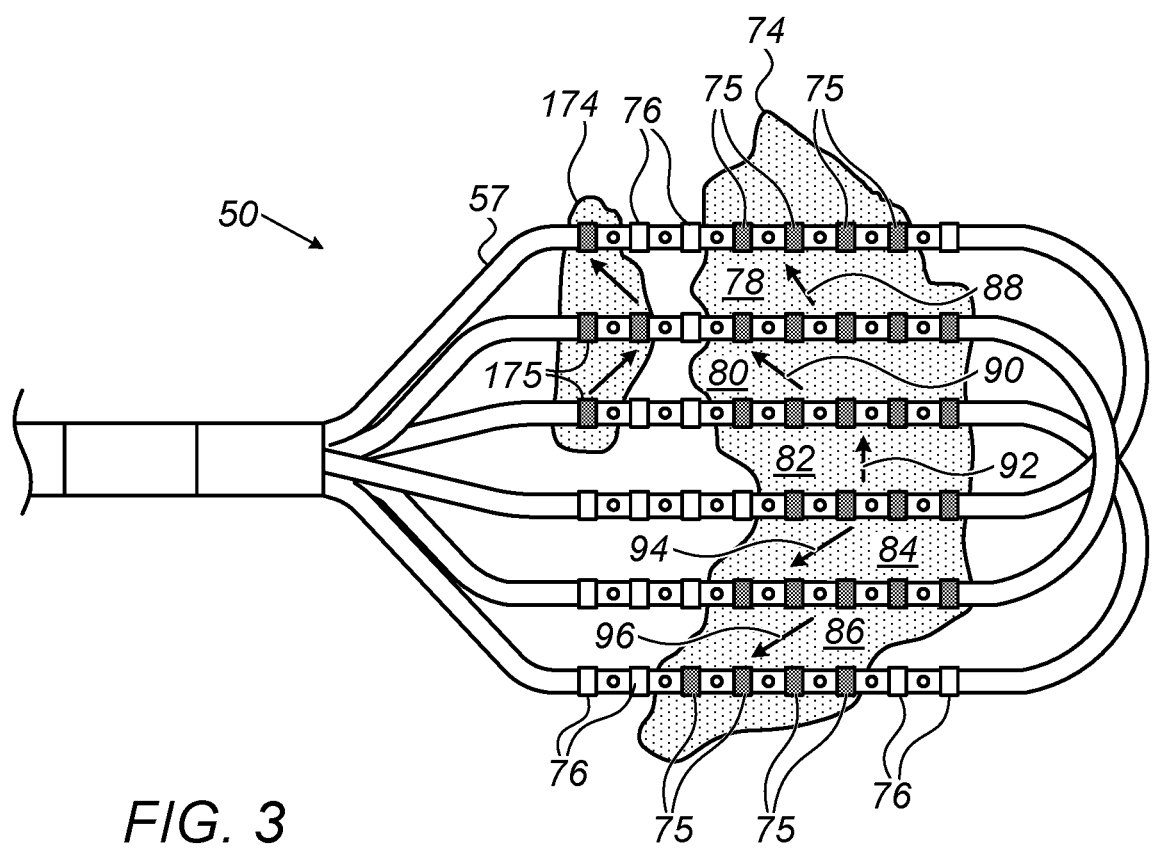
FIG. 3 is a side view of the flat array of multiple electrodes of FIG. 2 highlighting pairs of electrodes selected for irreversible electroporation (IRE) ablation, in accordance with an exemplary embodiment of the present invention.

FIG. 3 is a side view of flat array 50 of multiple electrodes 55 of FIG. 2 highlighting subsets of electrodes 75 and 175 selected for irreversible electroporation (IRE) ablation of separate tissue regions 74 and 174, respectively, in accordance with an exemplary embodiment of the present invention.

In the illustrated exemplary embodiment, processor 41 determines that the subsets of electrodes 75 and 175 of the electrode-array are in contact with tissue areas 74 and 174, for example, using one of the electrical, mechanical, or other available methods for determining physical contact of an electrode of a catheter with tissue. As seen, selected electrodes 75 and 175 are shaded in black, in contrast to electrodes 76 which are deemed to be not in contact with tissue. Processor 41 therefore selects electrodes 75 and 175, and subsequently commands switching assembly 38 to connect electrodes 75 and electrodes 175 to IRE pulse-generator 37 to apply bipolar IRE pulses between pairs of electrodes 75 and separately apply bipolar IRE pulses between pairs of electrodes 175. Nevertheless, if the two regions are close, the processor may unite electrodes 75 and 175 to determine a best electrode connection configuration for the IRE ablation.

Processor 41 is used to select an IRE ablation protocol comprising the bipolar IRE pulses. An example of IRE ablation settings that may be used with electrode 75 and 175 of catheter 21 is given by Table I:

TABLE I

| Parameter | Range |
| --- | --- |
| Preset IRE peak voltage | 500-2000 V |
| Pulse width | 0.5-10 microsecond |
| Repetition rate | 1-400 Hz |
| Number of pulses | 10-200 |
| Directon of electrical field | User selected |

As seen in the protocol of Table I, the direction of applied electric fields is user selected. FIG. 3 shows that physician 30 selected to apply the pulses such that different tissue regions 78, 80, 82, 84, and 86 in contact with electrodes 75 receive IRE pulses with the electric field oriented along directions 88, 90, 92, 94, and 96, respectively. Such a selection may, for example, suit known myocardium fiber cell alignment to selectively kill them. A possible means to enable a user to select electric field directions is a graphical user interface that inputs selected electric field directions to a processor to accordingly select pairs of electrodes 75 between which to apply pulses. However, other methods may be used, such as selecting one of a number of preset possible directions.

Figure 4:
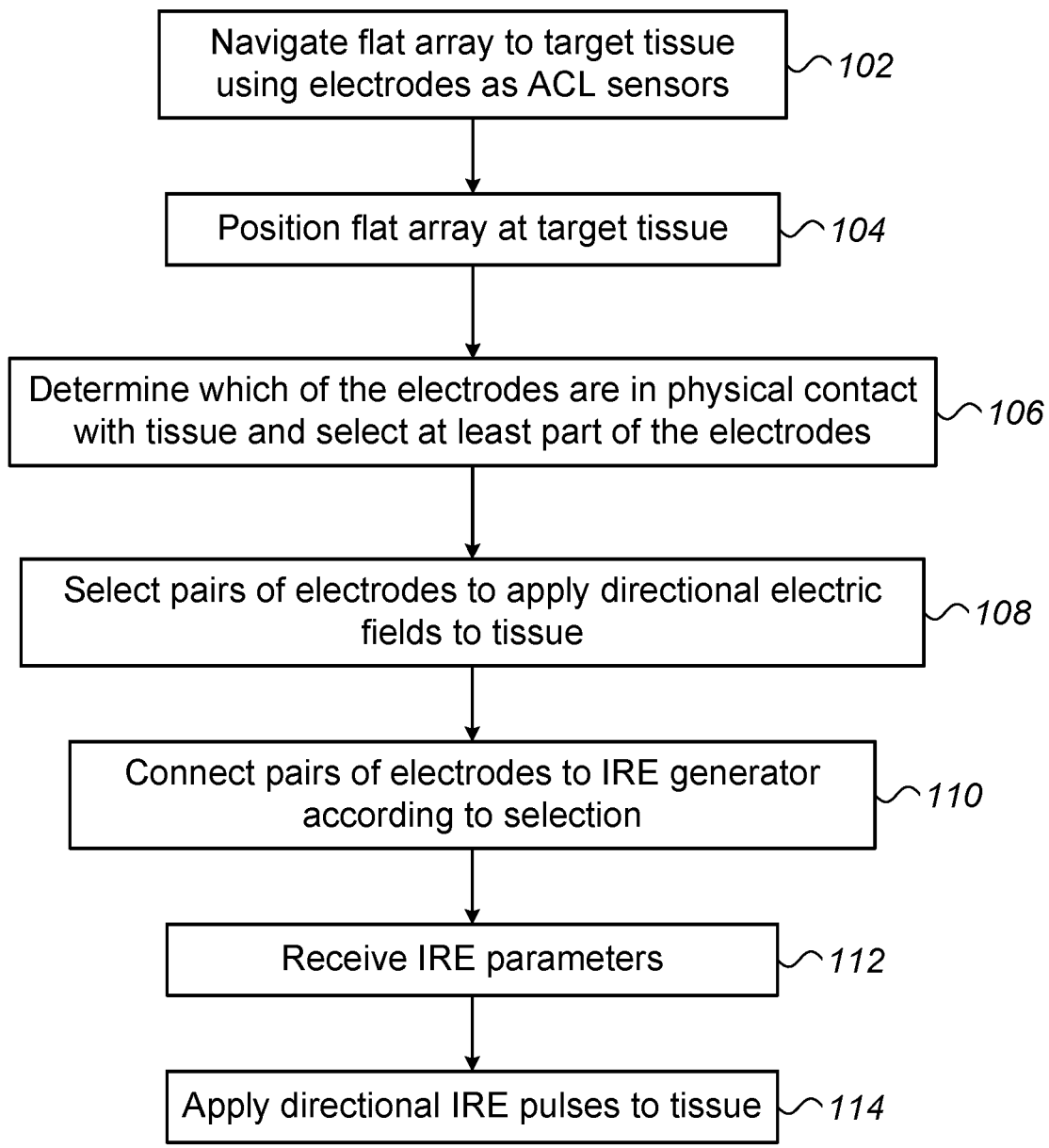
FIG. 4 is a flow chart that schematically illustrates a method of irreversible electroporation (IRE) using the flat array of multiple electrodes of FIG. 2, in accordance with an exemplary embodiment of the present invention.

FIG. 4 is a flow chart that schematically illustrates a method of applying irreversible electroporation (IRE) using flat array 50 of multiple electrodes 55 of FIG. 2, in accordance with an exemplary embodiment of the present invention. The algorithm, according to the presented embodiment, carries out a process that begins when physician 30 navigates flat array 50 to a target tissue location in an organ of a patient, such as at an ostium in the heart, for example, using, for example, electrodes 55 as ACL-sensing electrodes, at a flat array navigation step 102.

Next, physician 30 positions flat array 50 at ostium, at a flat array positioning step 104. Subsequently, processor 41 determines which of electrodes 55 are in contact with tissue and physician 30 selects at least part of these electrodes to apply IRE pulses, at an electrode physical contact determination and selection step 106.

Next, at an electrode configuration setup step 108, processor 41 receives user inputs, such as of step 106 and/or in the form of one or more prespecified directions (e.g., relative to a longitudinal axis of the distal end) along which the electric field should be applied to tissue. The prespecified directions may differ from one tissue region to another, as described above. Based on the required electric field directions, processor 41 determines the pairs of the selected electrodes to apply IRE pulses between.

Next, processor 41 controls switching assembly 38 to connect the pairs of electrodes to IRE pulse-generator 37 according to the determined configuration, at pair electrodes connecting step 110.

Processor 41 then receives (e.g., uploads from memory) an ablation protocol comprising the IRE ablation parameters (e.g., number and peak voltage of pulses), at an IRE parameter selection step 112. At this stage the physician may modify some of the parameters. Alternatively, the protocol may have been loaded earlier in the procedure and is ready at this stage.

Finally, processor 41 commands IRE pulse-generator 37 to apply the directional IRE pulses to tissue via the selected pairs of electrodes 55, at an IRE treatment step 114.

FIG. 4 is an example flow that is depicted purely for the sake of clarity. Additional steps may be included, such as applying irrigation. In alternative embodiments, any other suitable method flow can be used. For example, in the absence of sufficient information regarding myocardial cell orientations, processor 41 may control switching assembly to apply IRE pulses at multiple (typically two) different orientations to the same region of tissue. For example, processor 41 may control switching assembly 38 to apply the IRE pulses at two orthogonal directions.

Although the exemplary embodiments described herein mainly address cardiac applications, the methods and systems described herein can also be used in other medical applications, such as in neurology, otolaryngology, and renal denervation.

It will be thus appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for application of irreversible electroporation, comprising:
    inserting an array of electrodes, fitted at a distal end of a catheter, into a cavity in an organ of a patient;
    bringing at least a portion of the array into contact with tissue on an inner surface of the organ;
    visualizing to the user a visualization of the inner surface of the cavity, a position of the array relative to the cavity and the portion of the array that is in contact with the inner surface of the cavity;
    receiving, from a user, input that specifies one or more tissue segments to be ablated on the inner surface and a selected local orientation of an electric field that defines a direction of propagation of the electric field between at least one pair of electrodes in the array with respect to at least one of the one or more tissue segments, wherein the selected local orientation is indicated on the visualization of the inner surface of the cavity;
    using a processor, selecting in response to the input, one or more pairs of the electrodes in the array that, when driven with irreversible electroporation (IRE) signals, generate the electric field in the selected local orientation; and
    ablating the specified one or more tissue segments by applying the IRE signals to the one or more pairs of the electrodes.

2. The method according to claim 1, comprising receiving from the user a selected local orientation for each of the one or more tissue segments indicated.

3. The method according to claim 1, wherein bringing the array into contact with the inner surface of the cavity comprises measuring impedances using the multiple electrodes.

4. The method according to claim 1, wherein bringing the array into contact with the inner surface of the cavity comprises measuring a shape of the array.

5. The method according to claim 1, wherein bringing the array into contact with the inner surface of the cavity comprises measuring contact force between the array and the inner surface.

6. The method according to claim 1, wherein the array is a flat array.

7. The method of claim 1, wherein the selected local orientation is defined to selectively ablate cardiac cells in the specified tissue segment.

8. The method of claim 1, comprising:
    selecting in response to the input, a first pair of the electrodes in the array that, when driven with irreversible electroporation (IRE) signals, generates a first electric field in the selected local orientation and a second pair of the electrodes in the array that, when driven with irreversible electroporation (IRE) signals, generate a second electric field in an orientation orthogonal to the selected local orientation;

ablating the specified tissue segments by applying the IRE signals to each of the first pair and the second pair.

9. A system for application of irreversible electroporation, the system comprising:
- a processor, which is connected to an array of electrodes that is fitted at a distal end of a catheter, inserted into a cavity in an organ of a patient and brought into contact with an inner surface of the organ, the processor configured to:
- visualize to the user a visualization of the inner surface of the cavity, a position of the array relative to the cavity and the portion of the array that is in contact with the inner surface of the cavity;
- receive, from a user, input that specifies one or more tissue segments to be ablated on the inner surface and a selected local orientation of an electric field that defines a direction of propagation of the electric field between at least one pair of electrodes in the array with respect to at least one of the one or more tissue segments, wherein the selected local orientation is indicated on the visualization of the inner surface of the cavity in response to providing the visualized; and
- select one or more pairs of the electrodes in the array that, when driven with irreversible electroporation (IRE) signals, generate the electric field in the selected local orientation; and
- an IRE generator, which is configured to ablate the specified tissue segments by applying the IRE signals to the one or more pairs of the electrodes.

10. The system according to claim 9, wherein the processor is configured to receive from the user the selected local orientation in each of the one or more tissue segments indicated.

11. The system according to claim 9, wherein the array is a flat array.

12. The system of claim 9, wherein the selected local orientation is defined to selectively ablate cardiac cells in the specified tissue segment.

13. The system of claim 9, wherein the processor is configured to select a first pair of the electrodes in the array that, when driven with irreversible electroporation (IRE) signals, generates a first electric field in the selected local orientation and a second pair of the electrodes in the array that, when driven with irreversible electroporation (IRE) signals, generates a second electric field in an orientation orthogonal to the selected local orientation, and wherein the IRE generator, is configured to ablate the specified tissue segments by applying the IRE signals to each of the first pair and the second pair.

* * * * *